(12) United States Patent
König et al.

(10) Patent No.: US 6,413,970 B1
(45) Date of Patent: Jul. 2, 2002

(54) PHARMACEUTICAL COMPOSITION FOR TREATING VIRAL DISEASES

(75) Inventors: Brigitte König, Hagen (DE); Jean-Pierre Rihoux, Erpent (BE); Wolfgang König, Recklinghausen (DE)

(73) Assignee: UCB S.A., Brussels (BE)

( * ) Notice: Subject to any disclaimer, the term of this patent is extended or adjusted under 35 U.S.C. 154(b) by 0 days.

(21) Appl. No.: 09/254,548

(22) PCT Filed: Sep. 8, 1997

(86) PCT No.: PCT/EP97/04859

§ 371 (c)(1),
(2), (4) Date: Apr. 21, 1999

(87) PCT Pub. No.: WO98/10764

PCT Pub. Date: Mar. 19, 1998

(30) Foreign Application Priority Data

Sep. 11, 1996 (EP) .............................................. 96870114

(51) Int. Cl.$^7$ ............................................ A61K 31/505
(52) U.S. Cl. ....................................................... 514/256
(58) Field of Search ......................................... 514/255

(56) References Cited

U.S. PATENT DOCUMENTS 4,525,358 A * 6/1985 Balles et al. ................ 514/255

OTHER PUBLICATIONS

Fields Vinoley 3rd Ed fields et al Ed hippincoll—Raven Philadelphia pp 1313–1314.*
Tarayre et al 117CA: 103861.*

H.P. Heckert et al., "Klinische Hinweise auf eine unterstutzende Wirkung von Antihistaminika (Benadryl–parenteral) bej der Behandlung der RSV–Infektion des Rindes," "Zusammenfassung," BMTW (Germany), vol. 106, No. 7, 1993, pp. 230–235.

G.P. Anderson et al., "New drugs for asthma therapy", 1991, Birkhauser, Basel XP002025611 Bernheim, J. et al.: Cetirizine: More than an antihistamine?, pp. 269–293.

R.A. Wood et al., "Atopic disease, rhinitis and conjuctivitis, and upper respiratory infections", Current Opinion in Pediatrics, vol. 7, 1995, pp. 619–620.

R.C. Welliver, "The development of respiratory syncytial virus–specific igE and the release of histamine in nasopharyngeal secretions after infection", The New England Journal of Medicine, vol. 305, No. 15, 1981, pp. 841–846.

T. Chonmaitree et al., "Respiratory viruses induce production of histamine–releasing factor by mononuclear leukocytes: a possible role in the mechanism of virus–induced asthma", The Journal Of Infectious Diseases, vol. 164, No. 3, 1991, pp. 592–594.

* cited by examiner

*Primary Examiner*—Russell Travers
(74) *Attorney, Agent, or Firm*—Finnegan, Henderson, Farabow, Garrett & Dunner, L.L.P.

(57) ABSTRACT

Use of 2-[2-[4-[(4-chlorophenyl)phenylmethyl]-1-piperazinyl]ethoxy-acetic-acid, an individual optical isomer or a pharmaceutically acceptable salt thereof as an active ingredient for the production of a pharmaceutical composition for the treatment of diseases induced by the respiratory-syncytial-virus.

16 Claims, 4 Drawing Sheets

1 2 3 4 5 6 M 7 8 9 10 11 12 M

A)

← 2 h

M 1 2 3 4 5 6 7

B)

16 h

M 1 2 3 4 5 6 7

PHARMACEUTICAL COMPOSITION FOR TREATING VIRAL DISEASES

This application is a 371 application of PCT/EP98/04889 filed Sep. 8, 1997 which claims priority to EP Application 96870114 filed Sep. 11, 1996.

The present invention is in the area of pharmaceutical compositions and methods of treatment of viral diseases in humans. More particularly the invention relates to pharmaceutical compositions for the treatment of diseases induced by the respiratory-syncytial virus (RSV).

It is well known that recurrent respiratory tract viral infections are followed by rapid sensitization to one or several antigens with increased levels of immunoglobulins E, see e.g. Oscar L. FRICK in J. Allergy Clin. Immunol. (November 1986), pp. 1013–1018. Further, one dominant virus causing wheezing in humans and more especially in children is respiratory syncytial virus. The latter is especially observed in children below 2 years of age in whom it causes bronchiolitis and pneumonia.

T. CHONMAITREE et al. In Journal of Infections Diseases, vol. 164 (3), pp. 592–594 (1991) discloses that mononuclear leukocytes from normal individuals produce a histamine-releasing factor (HRF) in response to exposure to respiratory viruses, suggesting that this cytokine may play a role in the mechanism of virus-induced bronchospasm. However these authors have also shown that this HRF appears to be distinct from most other cytokines such as interleulkins-1–6, 8 and 9 or granulocytes.

R. C. WELLIVER et al. In New England Journal of Medicine vol. 305 (15), pp. 841–846 (1981) discloses that respiratory syncytial virus (RSV)-specific immunoglobulines E together with histamine are detectable in a majority of infants with various forms of respiratory illness due to RSV and showing wheezing. However a direct correlation of the titers of RSV-IgE with the quantity of histamine released could not be determined.

There are many theoretical mechanisms whereby viruses might induce or exacerbate an inflammation in the lower airways. In addition to alveolar macrophages, the peribronchiolar infiltration with neutrophilic granulocytes is observed after an infection with respiratory syncytial virus. Neutrophils are not only cells capable of phagocytosis and low molecular weight inflammatory mediator release, but they also have the potential to secrete multiple proinflammatory cytolines. Recently, new cytokines named chemokines were described as activating inflammatory cells, see for example Piotr KUNA in Pharmacia Allergy Research Foundation Award Book (1995) pp. 23–31. In this family of chemolines, interleukin-8 (IL-8) is a very potent chemotactic factor for polymorphonuclear cells. This chemokine, according to B. KÖNIG et al. in Journal of Leukocyte Biology (July 1996), is produced high amounts by human polymorphonuclear cells during exposure to respiratory syncytial virus. In another study published by R. ARNOLD at al. in Immunology, 85, 364–372 (1995), evidence is presented that peripheral blood mononuclear cells synthesize and secrete the proinflammatory cytokine IL-8 following infection with the respiratory syncytial virus (RSV) even at low doses. The authors of this study suggest that the release of the potent chemotoxin IL-8 from peripheral blood mononuclear cells might be responsible for the pronounced accumulation of polymorphonuclear granulocytes in the alveolar spaces during RSV-induced bronchiolitis.

H. P. HECKERT et aL In Berliner Münchner Tierärzl Wschr. Vol. 106 (7), pp. 230–235 (1993) discusses the treatment of Bovine RSV-infection. In addition to antibiotic therapy, the effect of treatment with the antihistamine diphenylhydramin was evaluated by measure of the internal body temperature. With the additional daily application of the antihistamine to the antibiotic therapy, the animals were significantly faster with fever. However the teaching of this document is strictly limited to bovines and, on the other hand, it fails to explain the respective mechanisms of action of each constituent of the prescribed combination.

From a therapeutic point of view, it must be pointed out that there is no specific treatment for curing respiratory syncytial virus infections. Moreover, it is well known that several drugs used for the treatment of allergy and asthma (corticosteroids, theophylline. ketotifen) display inhibiting effects on cells directly involved in the immune defense mechanisms thereby increasing the risk of microbial and viral infections.

Thus an objective of the present invention is to provide useful pharmaceutical compositions for treating diseases induced by the respiratory-syncytial virus in humans.

The present invention is based on the unexpected recognition that 2-[2-[4-[(4-chloropheny)phenylmethyl]-1-piperazinyl]ethoxy]-acetic acid, an individual optical isomer or a pharmaceutically acceptable salt thereof, displays a significant inhibiting effect on viral replication together with an inhibiting effect of RSV-induced cell modifications (IL-8 production). Moreover this pharmacological effect takes place without lowering the immune system of the patient.

This recognition demonstrates the existence of an unexpected protective effect obtained in treating diseases, such as acute bronchiolotis or viral pneumonia, induced by the respiratory syncytial virus in humans, by a method which comprises administering to a human in need of such therapy, a pharmaceutical composition comprising as an active ingredient, an effective amount of at least one compound selected from 2-[2-[4-[(4-chlorophenyl)phenylmethyl]-1-piperazinyl]ethoxy]-acetic acid, an individual optical isomer or a pharmaceutically acceptable salt thereof.

The term "pharmaceutically acceptable salt" as used herein with respect to 2-[2-[4-[(4-chlorophenyl) phenylmethyl]-1-piperazinyl]ethoxy]-acetic acid means not only its addition salts with non-toxic organic and inorganic acids, such as acetic, citric, succinic, ascorbic, hydrochloric, hydrobromic, sulfuric, and phosphoric acids and the like, but also its metal salts (for example sodium or potassium salts), ammonium salts including quaternary ammonium salts and aminoacid salts.

The term "individual optical isomer" as used herein means the levorotatory and the dextrorotatary enantiomers thereof. As is well known in the art, purification of such enantiomers is a rather difficult process depending upon the selected way of preparation of the compound and the optical purity of the starting material. Therefore the term "individual optical isomer" as used herein means that the said compound comprises at least 90%, preferably at least 95%, by weight of the said individual (either dextro- or levorotatory) optical isomer and at most 10%, preferably at most 5%, by weight of the other individual (respectively levo- or dextrorotatary) optical isomer. Each individual optical isomer may be obtained from its racemic mixture by using conventional means such as disclosed in British patent application No. 2,225,321. Additionally, each individual optical isomer can be prepared from the racemic mixture by enzymatic biocatalytic resolution, such as disclosed in U.S. Pat. Nos. 4,800,162 and 5,057,427.

The most preferred active ingredients of the present invention are the racemate of 2-[2-[4-[(4-chlorophenyl) phenylmethyl]-1-piperazinyl]ethoxy]-acetic acid and its dihydrochloride salt which is a histamine $H_1$ receptor antagonist well known as cetirizine dihydrochloride, and its levorotatory and dextrorotatory enantiomers.

For implementing the invention, the composition hereinabove described should contain an effective amount of 2-[2-[4-[(4-chlorophenyl)phenylmethyl]-1-peperazinyl] ethoxy]-acetic acid, a pharmaceutically acceptable salt or individual optical isomer thereof. An effective amount can be readily determined by the use of conventional techniques and by observing results obtained under analogous circumstance. In determining the effective amount, a number of factors are considered including, but not limited to: the species of patient; its size, age, and general health; the specific disease involved; the degree of or involvement or the severity of the disease; the response of the individual patient; the particular compound administered; the mode of administration; the bioavailability characteristics of the preparation administered; the dose regimen selected; and the use of concomitant medication.

An effective amount of 2-[2-[4-[(4-chlorophenyl) phenylmethyl]-1-piperazinyl]ethoxy]-acetic acid, its pharmaceutically acceptable salt or individual optical isomer thereof in the composition of the invention will generally vary from about 0.1 milligram per kilogram of body weight per day (mg/kg/day) to about 0.5 mg/kg/day. A posology (dose) of about 5 mg to about 50 mg, preferably once or twice per day, is preferred.

A composition according to the invention can be administered to a patient in any form or mode which makes the composition bioavailable in effective amounts, namely the oral route. For example, it can be administered orally, intanasally, or rectally. Oral administration is generally preferred. One skilled in the art of preparing formulations can readily select the proper form and mode of administration depending upon the particular characteristics of the disease state to be treated, the stage of the disease, and other relevant circumstances.

The compositions of the invention can comprise 2-[2-[4-[(4-chlorophenyl)phenylmethyl]-1-piperazinyl]ethoxy]-acetic acid, its pharmaceutically acceptable salt or individual optical isomer thereof alone or in combination with at least one pharmaceutically acceptable carrier or excipient, the proportion and nature of which are determined by the solubility and chemical properties of the composition selected, the chosen route of administration, and standard pharmaceutical practice.

The carrier material may be a solid, semi-solid, or liquid material which can serve as a vehicle or medium for the active ingredient. Suitable carrier materials are well known in the art. The pharmaceutical compositions of the invention may be adapted for oral use and may be administered to the patient in the form of tablets, capsules, powders, elixirs, syrups, solutions, suspensions, or the like. The pharmaceutical composition of the invention may also be adapted for rectal use and may then be administered to the patient in the form of suppositories.

The carrier material should be suitably selected with respect to the intended form of administration and consistent with conventional pharmaceutical practice. For instance, for oral administration in the form of tablets or capsules, the therapeutically active drug components may be combined with any oral non-toxic pharmaceutically acceptable inert carrier such as lactose or starch. Optionally, the pharmaceutical composition of the invention also contain a binder such as microcrystalline cellulose, gum tragacanth or gelatine, a disintegrating agent such as alginic acid, a lubricant such as magnesium stearate, a glidant such as colloidal silicon dioxide, a sweetening agent such as sucrose or saccharin, a coloring agent or a flavouring agent such as peppermint or methyl salicylate.

Because of their easy administration, tablets and capsules represent the most advantageous oral dosage unit form. If desired, tablets may be coated by standard aqueous or nonaqueous techniques with sugar, shellac or other entering coating agents. Desirably, each tablet or capsule contains from about 5 mg to about 50 mg of the active ingredient.

For the purpose of oral therapeutic administration, the compositions of the present invention may be incorporated into a solution or suspension. These preparations should contain at least 0.1% by weight of the active ingredient of the composition of the invention.

Such solutions or suspensions may also include one or more of the following adjuvants: a sterile diluent such as water for injection, physiologic saline solution, oils, polyethylene glycols, glycerine, propylene glycol or other synthetic solvents; antibacterial agents such as benzyl alcohol; antioxidants such as ascorbic acid or sodium bisulfite; chelating agents such as ethylene diaminetetraacetic acid; buffers such as acetates, citrates or phosphates and agents for adjusting of tonicity such as sodium chloride or dextrose. The preparation can be enclosed in ampoules, or multiple dose vials made of glass or plastic.

The invention is further defined by reference to the following examples describing in detail the compositions of the present invention, as well as their utility.

While this invention has been described and illustrated with reference to certain preferred embodiments thereof, those skilled in the art will appreciate that various changes, modifications and substitutions can be made therein without departing from the spirit of the invention. For example, effective dosages other than the preferred ranges set forth hereinabove with respect to the active ingredients may be applicable as a consequence of variations of the responsiveness of the human treated, severity of symptoms, dosage related adverse effects, if any observed and similar considerations. Accordingly, such expected variations or differences in the practice of the present invention and the results obtained are contemplated in accordance with the objects and practices of the present invention.

Materials and Methods

Buffer

The buffer used for washing the polymorphonuclear cells consisted of 137 mM NaCl, 8 mM $Na_2HPO_4$, 3 mM KCl, and 3 mM $KH_2PO_4$, pH 7.4 (modified Dulbecco's phosphate-buffered saline). For stimulation assays the cells were suspended in RPMI 1640 medium (Gibco BRL, Eggenstein, Germany).

Preparation of Polymorphonuclear (PMN) Neutrophilic Granulocytes

Human granulocytes were isolated from 200 ml of heparinized blood (15 U ml) from healthy donors separated on a Ficoll-metrizoate gradient followed by dextran sedimentation and washed twice at 300 g. This method led to more than 95% pure PMN. The cells were diluted to a final density of $1\times10^6$ PMN.

Cell Viability

Cell viability was studied by trypan blue exclusion, by analysis of lactate dehydrogenase (Boehringer, Mannheim, Germany), as well as by determination of mitochondrial activity using WST-1 (Boehringer, Mannheim, Germany) in stimulated and non-stimulated cells. The assays were performed as described by the manufacturer (Boehringer, Mannheim, Germany). All experiments were performed under conditions where the viability of the cell types in all three assays systems was greater than 80%.

Cell Culture

Hep-2 epithelial cells, an epithelial tumor cell line, were obtained from the American Type Culture Collection as ATCC CCL 23 and were cultured at 37° C. in 5% carbon dioxide in Dulbecco's modified eagle containing 5% heat-inactivated fetal bovine serum, 4 mM L-glutamine and 80 μg/ml gentamicin. The cells were subcultured twice weekly.

Virus Preparation

Virus preparation was performed as described by R. ARNOLD et al. in Immunology 82, 126–133 (1994). For crude preparation, respiratory syncytial virus (RSV), Long Stain (ATCC), was grown and titrated in HEP-2 cells. The RSV titre was determined in a plaque-forming unit (PFU) assay. The stock titre of the virus pool used in the study was $5 \times 10^6$ PFU/ml. The stock solution was stored at −70° C. until use. Interleukin-8 (IL-8) levels were under the detection limit in the stock solution, as analysed by enzyme-linked immuno sorbent assay (ELISA). The absence of mycoplasma infection was verified by microplasma-specific PCR.

Stimulation Experiments

If not stated otherwise, human PMN ($1 \times 10^6$/ml) are treated with various amounts of RSV ($10^{3-10^7}$) plaque forming units [PFU] corresponding to a multiplicity of infection [m.o.i.] of 0.001 up to 10 in a volume of 1 ml RPMI-1640 medium for the indicated time intervals. The incubation was performed in the absence or in the presence of cetirizine dihydrochloride at the indicated concentrations. The cell supernatant of the stimulation experiments were collected by centrifugation and stored at −70° C. until use for analysis. The cell supernatants were used for IL-8 determination; cell pellets were for $RSV_{SH}$ genomic ribonucleic acid (RNA) detection.

IL-8 Assay

PMN were suspended in RPMI medium at a concentration of $1 \times 10^6$/ml. The cells were cultured in the presence of the appropriate stimulus for up to 24 hours. Culture supernatants were collected and analyzed for their IL-8 content. IL-8 release was determined using a sandwich ELISA according to the method indicated hereinbefore. In brief each well of a 96 well plate (Nunc Maxisorb, Roskilde, Denmark) was coated overnight at 4° C. with 100 μl of buffer/polyoxyethylene sorbitan monolaurate (a product sold under the tradename TWEEN 20) (0.1%) containing anti IL-8 antibodies at a concentration of 5 μg/ml. The plates were washed three times with buffer/Tween, the appropriate samples of IL-8 standard (recombinant human IL-8; Calbiochem, Bad Soden, Germany) were added and incubation proceeded for 2 hours at 37° C. Thereafter, alkline phosphatase-linked anti IL-8 antibody was added. After addition of p-nitrophenylphosphate (15 mg/ml) for quantification, an ELISA reader and for calculation Mikrotek software (SLT Labinstruments, Crailsheim, Germany) were used.

Analysis of Genomic RSV-RNA

The analysis of RSV-specific genomic RNA was performed by coupled reverse transcription and polymerase chain reaction PCR detection of RSV-genomic-RNA encoding for the small hydrophobic protein (SH) of RSV as described previously by R. ARNOLD et al. in Immunology 82, 126–133 (1994). Total RNA from non-infected as well as from RSV-infected PMN ($1 \times 10^6$/ml) was extracted using Trizol (Gibco, Niedereggenstein, Germany). Total RNA was dissolved in 30 μl $H_2O$. Expression of genomic $RSV_{SH}$ RNA was analysed after reverse transcription with sense primers and PCR amplification of the cDNA transcripts. The reverse transcription step involved a reaction mixture (final volume 20 μl) containing 10 mM Tris-HCl (pH 8.3), 50 mM KCl, 5 mM $MgCl_2$, 1 mM desoxynucleotides, 100 pM sense primers for $RSV_{SH}$, 10 U RNAse inhibitor, 10 μl RNA sample and 200 U reverse transcriptase from Moloney-Murine-leukemia-virus (Gibco, Eggenstein, Germany). Reverse transcription reactions were performed at 37° C. for 60 minutes. For PCR amplification of the cDNA products, reaction mixtures were mixed with 50 pM of sense and antisense primers and 2 U Taq Polymerase (Gibco, Eggenstein, Germany). The products of 20, 25, and 30 cycles (1 min, 94° C.; 2 min. 53° C.; 3 min, 72° C.) were analysed on an agarose gel and visualised by ethidium bromide staining. The respective primers for $RSV_{SH}$ were sense: 5'-ACCAATGGAAAATACATCC-3'; antisense: 5'-TGAATGCTATGTGTTG-3'. The predicted size of the amplified product was 204 base pairs for $RSV_{SH}$ according to R. ARNOLD et al. already cited.

BRIEF DESCRIPTION OF THE DRAWINGS

Statistical Analysis

Effects of Cetirizine on RSV-specific mRNA Synthesis

Figure 1:
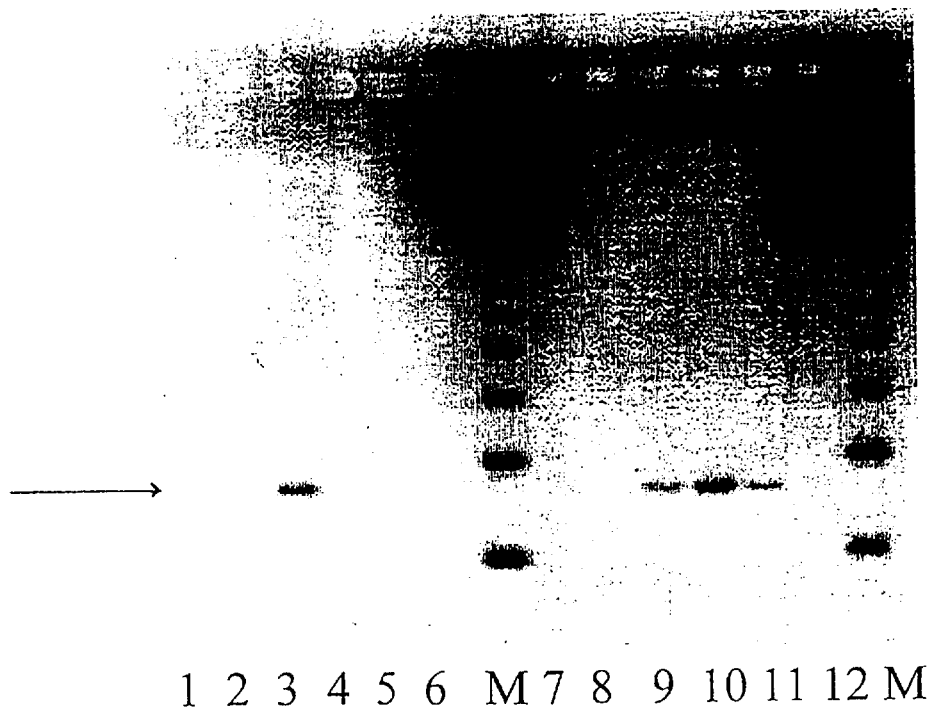
FIG. 1 shows RSV-specific mRNA expression

Recently, we have shown that RSV-specific genomic RNA resides inside PMNs up to 24 hours. We analyzed the effects of cetirizine on RSV-specific mRNA expression after stimulation of human PMN with RSV. Therefore, in a first set of experiments human PMN ($1 \times 10^6$/ml) were treated with RSV at a m.o.i. of 1-, 0.5-, 0.05-, 0.005-, for 2 hours as well as for 16 hours. The results of these experiments are shown in FIG. 1: Human PMN ($1 \times 10^6$/ml) were left untreated (lanes 1,2 and 7,8) or were treated with RSV (1 m.o.i.: lanes 3,9;0.5 m.o.i.: lanes 4,10; 0.05 m.o.i.: lanes 5,11; 0.005 m.o.i.: lanes 6,12) for 2hours (lanes 1–6) as well as for 16 hours (lanes 7–12) at 37° C. Cell pellets were analyzed for RSV-specific mRNA expression of the SH gene. The arrow indicates the amplified PCR product. M: 123 base pairs ladder (Gibco BRL, Eggenstein, Germany). FIG. 1 shows that RSV-specific mRNA increases inside PMN with prolonged incubation time.

Figure 2:
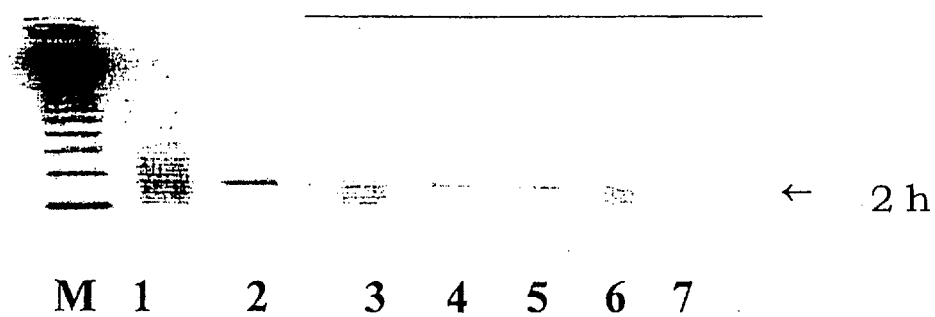
FIG. 2 shows RSV-specific mRNA expression treatment and control cells
Figure 2:
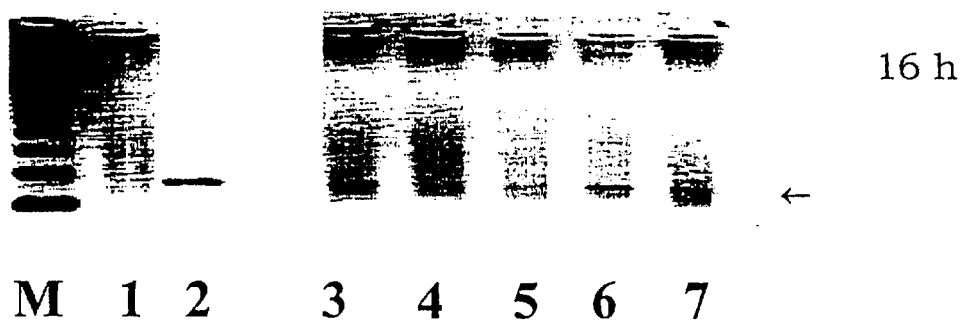

Next, human PMN ($1\times10^6$/ml) were treated with RSV at a m.o.i. of 1 in the absence or in the presence of cetirizine. The results of these experiments are shown in FIG. 2: human PMN were left untreated (lane 1) or were treated with RSV (1 m.o.i.) in the absence (lane 2) or in the presence of cetirizine (lanes 3–7;100-, 10-, 1-, 0.1-, 0.01 μg/$10^6$ PMN). Incubation proceeded for 2 hours (FIG. 2A) as well as for 16 hours (FIG. 2B) at 37° C. The cell pellets were analyzed for RSV-specific mRNA of the RSV-SH-gene by RT-PCR. The arrow indicates the amplified product of the appropriate size. M: 123 base pairs ladder (Gibco BRL, Eggenstein, Germany). FIG. 2 shows that the addition of cetirizine inhibits RSV-specific mRNA expression of the small hydrophobic (SH) gene. A decrease in RSV-specific mRNA expression was observed over the whole concentration range of cetirizine. Moreover a decrease in RSV-specific mRNA is indicative for a decrease in replicative virus. It should be noticed that such viral replication inhibition by an antihistamine was never observed before.

Figure 3:
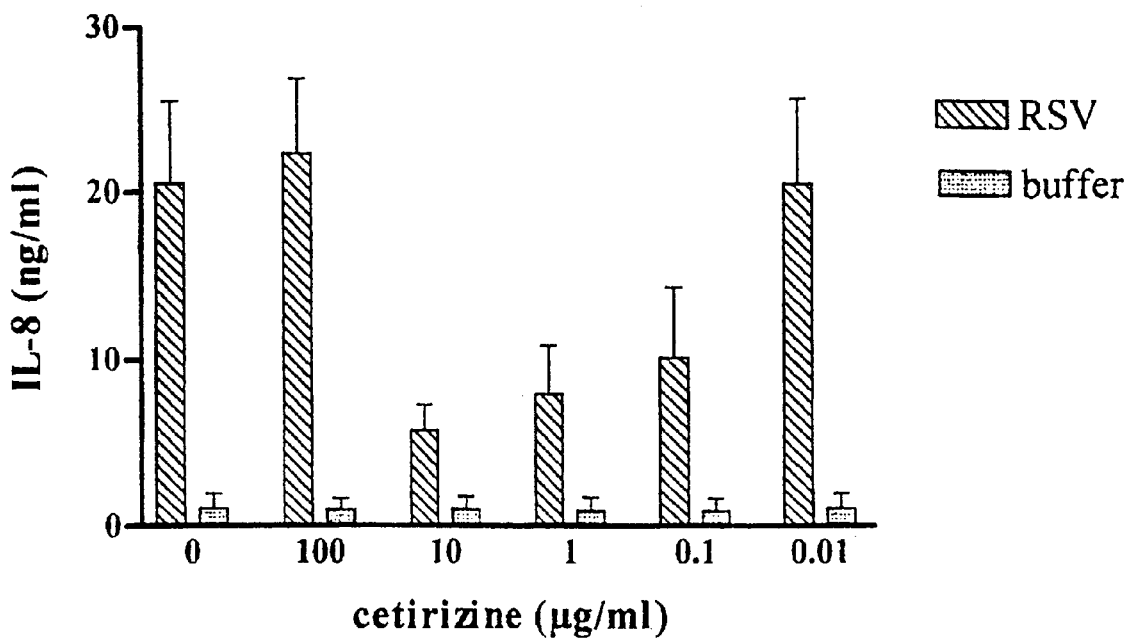
FIG. 3 shows RSV induced IL-8 release from human PMN cells

Effects of Cetirizine Dihydrochloride on RSV-induced IL-8 Release from Human PMN Human PMN ($1\times10^6$/ml) were treated with RSV at a multiplicity of infection (m.o.i.) of 0.01 μg/1ml) for a total incubation time of 2 hours at 37° C. As control, cells were tread with cetirizine (100-, 10-, 1-, 0.1-, 0.01-μg/ml) or without cetirizine, in the absence of RSV (buffer control). Cell supernatants were analyzed for IL-8 release by ELISA. The results of these experiments are shown in FIG. 3: data present mean and standard deviation values from 8 independent experiments. FIG. 3 shows that cetirizine dihydrochloride (hereinafter "cetirizine")down-regulated the RSV-induced IL-8 release. However, the effects of cetirizine were dose-dependent. In this regard, cetirizine at concentrations <0.01 μg/ml but >100 μg/ml led to a significant reduction in RSV-induced IL-8 release. Similar results were obtained after an incubation time up to 24 hours as well as at RSV concentrations up to 5 m.o.i. It should be notice that such interference between an antihistamine and an IL-8 induction by RSV was never observed before.

Effects of Cetirizine on the Ongoing IL-8 Release Induced by RSV

Figure 4:
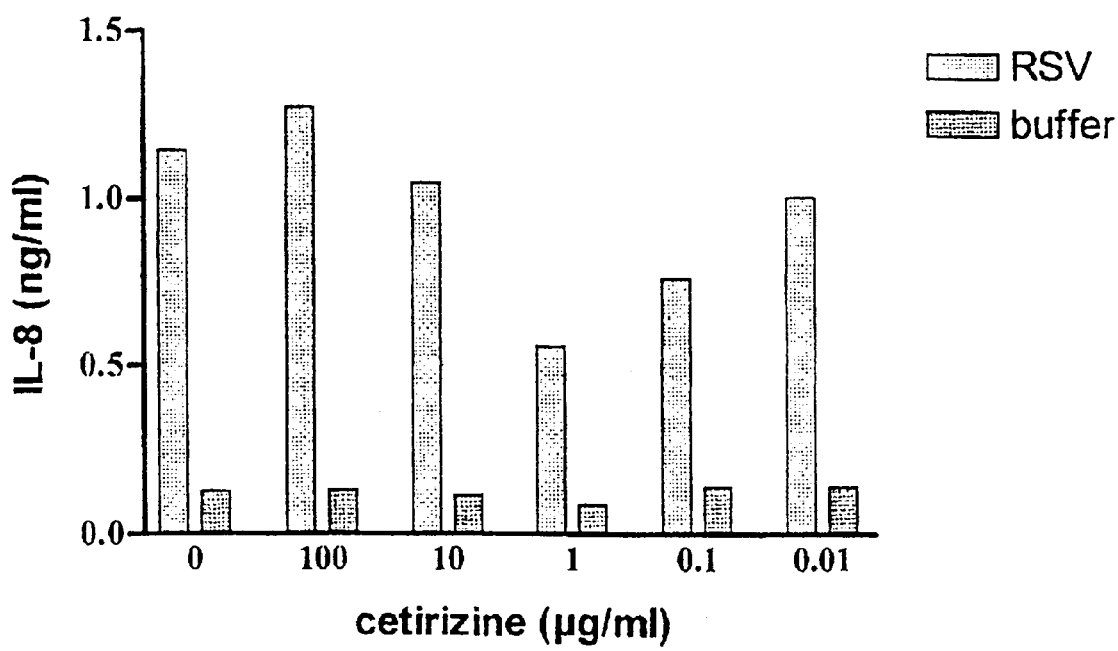
FIG. 4A shows IL-8 release with cetirizine addition immediately after RSV treatment
FIG. 4B shows IL-8 release with cetirizine addition 30 minutes after RSV treatment
FIG. 4C shows IL-8 release with cetirizine addition 60 minutes after RSV treatment
FIG. 4D shows IL-8 release with cetirizine addition 90 minutes after RSV treatment If not stated otherwise, all data show mean values of at least three individual experiments with cells from different donors.
Figure 4:
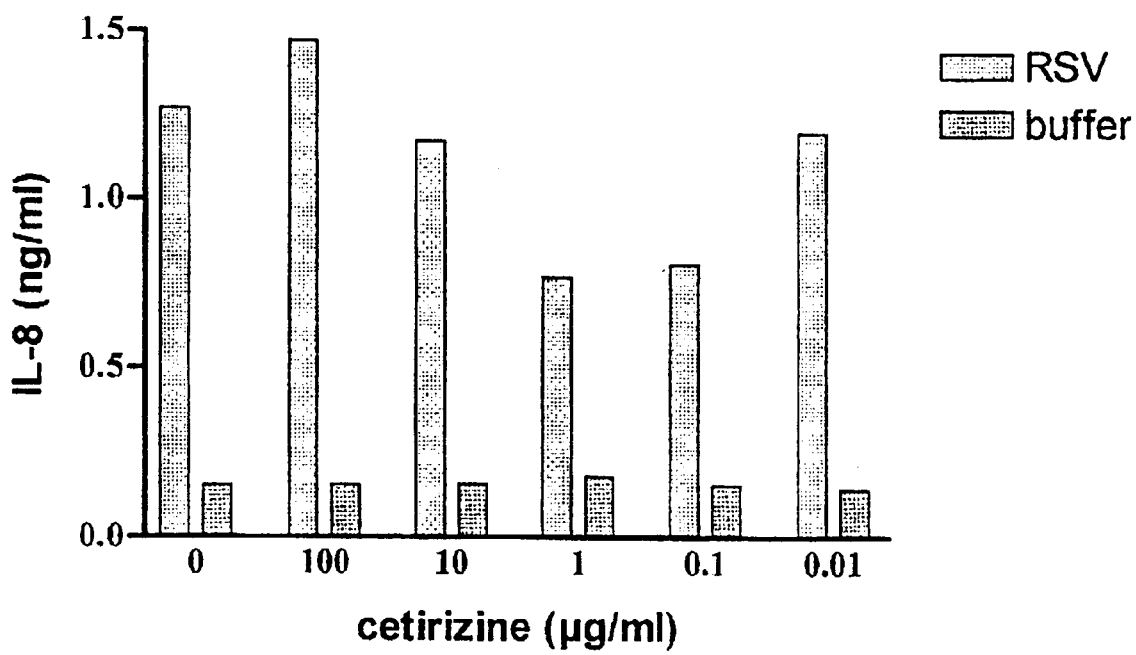
Figure 4:
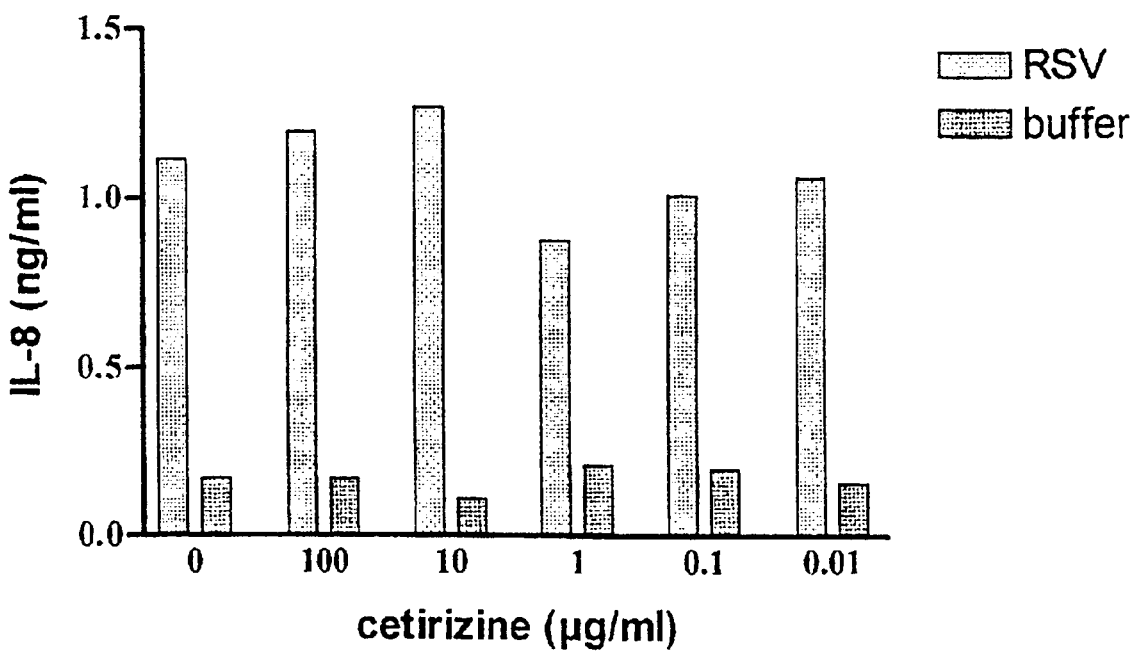
Figure 4:
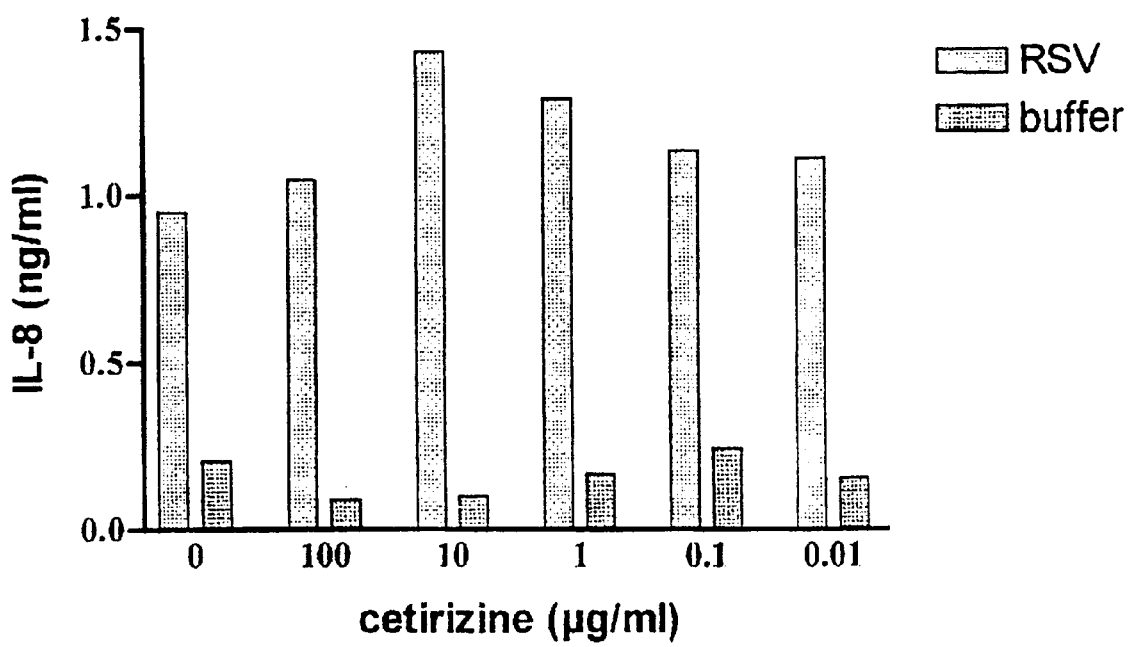

Further experiments were performed to analyze the effects of cetirizine on an ongoing IL-8 release induced by RSV. Therefore, human PMN ($1\times10^6$/ml) were treated with RSV (1 m.o.i.) and cetirizine (100 μg 10 μg, 0.01 μg). Cetirizine either added immediately (FIG. 4A), or 30 minutes (FIG. 4B), or 60 minutes (FIG. 4C), or 90 minutes (FIG. 4D) after onset of RSV treatment; a total incubation time of 2 hours at 37° C. was chosen. Cell supernatant were analyzed for IL-8 release by ELISA. Our data show that cetirizine down regulates an ongoing IL-8 release by RSV. However, the most pronounced effects were observed when cetirizine was added at the onset of RSV treatment. Down regulation of RSV-induced IL-8 release was most pronounced at cetirizine concentrations >0.01 μg/ml and <10 μg/ml.

What is claimed is:

1. A method for the treatment of a respiratory-syncytial-virus infection, comprising administering to a human in need of the treatment an effective amount of 2-[2-[4-[(4-chlorophenyl)phenylmethyl]-1-piperazinyl]ethoxy]-acetic acid, an individual optical isomer or a pharmaceutically acceptable salt thereof, as an active ingredient in a pharmaceutical composition.

2. The method according to claim 1, wherein the active ingredient is contained in the pharmaceutical composition, in a dose of from 5 mg to 50 mg.

3. The method according to claim 1, wherein the respiratory-syncytial-virus infection has caused acute brochiolitis or viral pneumonia.

4. The method according to claim 2, wherein the pharmaceutical composition further comprises at least one pharmaceutically acceptable carrier or excipient.

5. The method according to claim 1, wherein the pharmaceutical composition is administered orally.

6. The method according to claim 2, wherein the pharmaceutical composition is administered orally.

7. The method according to claim 3, wherein the pharmaceutical composition is administered orally.

8. The method according to claim 4, wherein the pharmaceutical composition is administered orally.

9. The method according to claim 4, wherein the pharmaceutical composition is in the form of tablets, capsules, powders, elixirs, syrups, solutions or suspensions.

10. The method according to claim 1, wherein the pharmaceutical composition is administered rectally.

11. The method according to claim 2, wherein the pharmaceutical composition is administered rectally.

12. The method according to claim 3, wherein the pharmaceutical composition is administered rectally.

13. The method according to claim 4, wherein the pharmaceutical composition is administered rectally.

14. The method according to claim 10, wherein the pharmaceutical composition is in the form of suppositories.

15. The method of claim 9, wherein the pharmaceutical composition is in the form of a solution or suspension containing at least 0.1% by weight of the active ingredient.

16. A method of inhibiting the replication of respiratory-syncytial-virus comprising administering to a host, 2-[2-[4-[(4-chlorophenyl)phenylmethyl]-1 piperazinyl]ethoxy]-acetic acid, an individual optical isomer or a pharmaceutically acceptable salt thereof.

* * * * *

UNITED STATES PATENT AND TRADEMARK OFFICE
CERTIFICATE OF CORRECTION

PATENT NO. : 6,413,970 B1  Page 1 of 1
DATED : July 2, 2002
INVENTOR(S) : König et al.

It is certified that error appears in the above-identified patent and that said Letters Patent is hereby corrected as shown below:

<u>Column 8,</u>
Lines 18-19, "brochiolitis" should read -- bronchiolitis --.
Line 49, "[(4-chlorophenyl)phenylmethyl]-1 piperazinyl]ethoxy]-" should read -- [(4-chlorophenyl)phenylmethyl]-1-piperazinyl]ethoxy]- --.

Signed and Sealed this

Nineteenth Day of November, 2002

*Attest:*

*Attesting Officer*

JAMES E. ROGAN
*Director of the United States Patent and Trademark Office*